(12) United States Patent
Gerlitz et al.

(10) Patent No.: US 10,376,189 B2
(45) Date of Patent: Aug. 13, 2019

(54) SUBSTANCE CONCENTRATION CORRECTION SYSTEMS AND METHODS

(71) Applicant: GlucoVista, Inc., Fairfield, NJ (US)

(72) Inventors: Yonatan Gerlitz, Herzliya (IL); Alexander Ostritsky, Rishon le Zion (IL); Rotem Gerlitz, Herzliya (IL)

(73) Assignee: GlucoVista, Inc., Fairfield, NJ (US)

( * ) Notice: Subject to any disclaimer, the term of this patent is extended or adjusted under 35 U.S.C. 154(b) by 536 days.

(21) Appl. No.: 15/072,090

(22) Filed: Mar. 16, 2016

(65) Prior Publication Data

US 2016/0270702 A1    Sep. 22, 2016

Related U.S. Application Data

(60) Provisional application No. 62/133,787, filed on Mar. 16, 2015.

(51) Int. Cl.
*A61B 5/1455* (2006.01)
*A61B 5/145* (2006.01)
(Continued)

(52) U.S. Cl.
CPC ........ *A61B 5/1455* (2013.01); *A61B 5/14532* (2013.01); *A61B 5/7203* (2013.01);
(Continued)

(58) Field of Classification Search
CPC . A61B 5/14532; A61B 5/1455; A61B 5/7203; A61B 5/7278; A61B 5/7246;
(Continued)

(56) References Cited

U.S. PATENT DOCUMENTS 4,907,895 A * 3/1990 Everest ............... G01J 5/62
356/43
6,515,285 B1    2/2003 Marshall et al.
(Continued)

FOREIGN PATENT DOCUMENTS

WO    2005015143 A2    2/2005

OTHER PUBLICATIONS

International Search Report and Written Opinion for International Application No. PCT/US2016/022700 dated Jun. 20, 2016.
(Continued)

*Primary Examiner* — Eric F Winakur
*Assistant Examiner* — Abid A Mustansir
(74) *Attorney, Agent, or Firm* — Randall Danskin P.S.

(57) ABSTRACT

A concentration correction system includes an infrared detector and components that produce an aggregate emission of infrared radiation. A mirror assembly includes a mirror and is changeable between a correcting configuration and a measuring configuration. In the correcting configuration, the mirror produces a mirror signal incident on the detector. The mirror assembly also obstructs external body infrared radiation from reaching the detector. In the measuring configuration, the mirror assembly allows the external body infrared radiation onto the detector. A concentration correction method includes receiving external body infrared radiation and simultaneously receiving a first portion of the aggregate emission. A measurement value indicative of concentration is recorded from the detector. A second portion of the aggregate emission reflected with the mirror and produces a mirror signal incident on the detector. A correction value corresponding to the mirror signal is recorded from the detector and used to correct the measurement value.

18 Claims, 2 Drawing Sheets

(51) Int. Cl.
  *A61N 5/00*  (2006.01)
  *G01J 3/02*  (2006.01)
  *G01J 3/08*  (2006.01)
  *G01J 3/10*  (2006.01)
  *G01J 5/00*  (2006.01)
  *A61B 5/00*  (2006.01)

(52) U.S. Cl.
  CPC .......... *A61B 5/7246* (2013.01); *A61B 5/7278* (2013.01); *G01J 3/021* (2013.01); *G01J 3/0294* (2013.01); *G01J 3/08* (2013.01); *G01J 3/108* (2013.01); *A61B 2562/0233* (2013.01); *G01J 3/0291* (2013.01); *G01J 2005/0048* (2013.01)

(58) Field of Classification Search
  CPC . A61B 2562/0233; A61B 5/0008; A61B 5/01; A61B 5/015; A61B 5/0059; G01J 2005/0048; G02B 7/1822; G02B 7/198; G02B 7/1827
  See application file for complete search history.

(56) References Cited

U.S. PATENT DOCUMENTS

| | | | | |
|---|---|---|---|---|
| 2010/0121170 A1* | 5/2010 | Rule | .................... | A61B 5/1427 600/365 |
| 2011/0004080 A1* | 1/2011 | Gerlitz | ................. | A61B 5/1491 600/316 |
| 2013/0090537 A1* | 4/2013 | Schemmann | ........ | A61B 5/1455 600/316 |
| 2013/0292571 A1* | 11/2013 | Mukherjee | .............. | G01J 3/108 250/339.11 |

OTHER PUBLICATIONS

Written Opinion for International Application No. PCT/US2009/037829; Publisher: Korean Intellectual Property Office dated Nov. 2, 2009.
International Search Report for International Application No. PCT/US2010/050901 dated Mar. 23, 2011.
International Search Report for International Application No. PCT/US2011/51218 dated Jan. 26, 2012.
US Patent and Trademark Office; Final Office Action for U.S. Appl. No. 112/607,903 dated Apr. 30, 2013.
US Patent and Trademark Office; Office Action for U.S. Appl. No. 12/883,063 dated Jan. 30, 2013.
US Patent and Trademark Office; Non-Final Office Action for U.S. Appl. No. 12/607,903 dated Nov. 27, 2012.
International Search Report and Written Opinion of International Application No. PCT/US2010/050901 dated Mar. 23, 2011.
International Searching Authority; International Search Report and Written Opinion for International Application No. PCT/US2015/036786 dated Sep. 15, 2015.
International Search Report for International Application No. PCT/US2011/051218 dated Jan. 26, 2012.
US Patent and Trademark Office, Non-Final Office Action for U.S. Appl. No. 12/883,063 dated Oct. 9, 2013.
US Patent and Trademark Office, Final Office Action for U.S. Appl. No. 12/883,063 dated Jun. 18, 2013.
State Intellectual Property Office of China; Office Action for CN Application No. 201080048921.5 dated Feb. 19, 2014.
Office Action issued in U.S. Appl. No. 13/841,911 dated May 29, 2014.
State Intellectual Property Office of China; Office Action issued in Chinese Patent Application No. 201180043984.6 dated Jun. 3, 2014.
Canadian Intellectual Property Office, Office Action issued in CA Patent Application No. 2779382 dated May 22, 2014.
Office Action Issued in U.S. Appl. No. 12/883,063 dated Apr. 4, 2014.
State Intellectual Property Office of China; Office Action Issued in Chinese Patent Application No. 201180043984.6 dated Jun. 6, 2014.
Extended EP Search Report for International Application No. PCT/US2011051218 dated Jun. 25, 2014.
State Intellectual Property Office of China; Office Action for CN Application No. 201080048921.5 dated Nov. 24, 2014.
US Patent and Trademark Office; Office Action for U.S. Appl. No. 12/883,063 dated May 13, 2015.
State Intellectual Property Office of China; Office Action for CN Application No. 201080048921.5 dated Jul. 29, 2015.
Yeh S-J et al: "Monitoring Blood Glucose Changes in Cutaneous Tissue by Temperature-Modulated Localized Reflectance Measurements", Clinical Chemistry, Washington, DC vol. 49, No. 6, pp. 924-934 Jun. 1, 2003.

* cited by examiner

SUBSTANCE CONCENTRATION CORRECTION SYSTEMS AND METHODS

CROSS REFERENCE TO RELATED APPLICATIONS

This application claims the benefit of priority under 35 U.S.C. § 119 to U.S. Provisional Patent Application No. 62/133,787, filed on Mar. 16, 2015 and entitled "Systems and Methods for Correcting Non-Invasive Substance Concentration Signal Measurements," which is incorporated herein by reference.

BACKGROUND

Spectroscopic techniques using infrared ("IR") radiation are known and have been widely described for use in non-invasive measurement of the concentration of substances of interest in a body. One area of interest includes the use of such techniques for the non-invasive measurement of the concentration of glucose in blood, whether human or animal. Several patents and patent applications disclose methods to non-invasively measure the concentration of a substance, such as glucose, for example, in the human bloodstream using infrared detection systems and methods.

U.S. patent application Ser. No. 12/883,063, filed Sep. 15, 2010 and entitled "Method for non-invasive analysis of a substance concentration within a body," describes methods of measuring a concentration of a substance, such as glucose, in a body. The described methods include changing the temperature of the surface of a body from a first temperature to a second temperature, then changing the temperature of the surface of the body from the second temperature back to the first temperature. The method includes measuring a first amount of infrared ("IR") radiation absorbed or emitted from the surface of the body in a first wavelength band and a second amount of IR radiation absorbed or emitted from the surface of the body in a second wavelength band at predetermined time intervals. The measurements occur during the time period that the temperature of the surface of the body changes from the second temperature back to the first temperature. A concentration of the substance may be determined based on the measurements. The contents of U.S. patent application Ser. No. 12/883,063 are incorporated herein by reference.

SUMMARY

A substance concentration correction system includes an infrared radiation detector having a sensitive area that receives infrared radiation from a body external to the correction system. The system also includes components that produce an aggregate emission of infrared radiation, a first portion of the aggregate emission being incident on the sensitive area. The system further includes a mirror assembly including a mirror and being changeable between a correcting configuration and a measuring configuration. Thus, in the correcting configuration, a second portion of the aggregate emission is reflected by the mirror, which produces a mirror signal incident on the sensitive area. The mirror assembly also obstructs the external body infrared radiation from reaching the sensitive area. In the measuring configuration, the mirror assembly allows the external body infrared radiation onto the sensitive area.

A substance concentration correction method includes providing a substance concentration correction system having an infrared radiation detector having a sensitive area, components that produce an aggregate emission of infrared radiation, a mirror assembly including a mirror. The method includes placing the mirror assembly in a measuring configuration. As enabled by the measuring configuration, the method includes receiving infrared radiation on the sensitive area from a body external to the correction system and simultaneously receiving a first portion of the aggregate emission on the sensitive area. A measurement value corresponding to the external body infrared radiation combined with the first portion of the aggregate emission is recorded from the detector. The measurement value is indicative of a substance concentration.

The method includes placing the mirror assembly in a correcting configuration. As enabled by the correcting configuration, the method includes reflecting a second portion of the aggregate emission with the mirror, which produces a mirror signal incident on the sensitive area, and the mirror assembly simultaneously obstructing the external body infrared radiation from the sensitive area. A correction value corresponding to the mirror signal is recorded from the detector. The method includes correcting the measurement value based on the correction value and calculating the substance concentration based on the corrected measurement value.

BRIEF DESCRIPTION OF THE DRAWINGS

Some embodiments are described below with reference to the following accompanying drawings.

DETAILED DESCRIPTION

Over the last 20 years, many attempts have been made to develop a marketable non-invasive glucose meter using infrared (IR) radiation. Developing a marketable non-invasive glucose meter may be difficult due to the impact on measurement accuracy of various perturbations in IR radiation emissions involved in the measurement of both reference signals and body signals. For example, when measuring IR radiation emission from a blackbody and from humans, various perturbations in the signal may occur.

Systems and methods herein correct non-invasive substance concentrations to overcome one or more of the above listed deficiencies. Measurements of the concentration of a substance may be modified or otherwise adjusted to account for perturbations in raw measurement data. The adjustments may be based on infrared measurements of a mirror. For example, the described perturbations may be corrected by measuring the aggregate IR radiation emission from various components of a system that is reflected from a mirror to an IR detector. The mirror measurement may be taken immediately after each concentration signal measurement to enhance the accuracy of the correction. The mirror reflection measurements may be used to correct non-invasive substance concentration signal measurements, such as measurements taken in the Mid-Infrared (MIR) region where infrared spectra exhibit wavelengths of about 6 to about 15 micrometers (μm).

The systems and methods described herein may be used in wearable non-invasive substance concentration systems and methods. Examples of such systems and methods are described in U.S. patent application Ser. No. 14/745,180 filed Jun. 19, 2015 (hereinafter, "180 Application"), which application is incorporated herein by reference in its entirety. Consequently, MIR detector assembly 130 of the '180 Application may be further configured to measure the MIR emission of a mirror.

In order to measure a concentration of a substance, such as glucose, in a body, two filters may be used. Although the present document refers often to glucose concentration, it will be understood that the systems and methods herein may apply to measuring the concentration of other substances. One filter may pass wavelengths where the substance has peak emission/absorption and the second filter may pass wavelengths where the substance has a negligible emission/absorption or no emission/absorption. The two measurements may be normalized against blackbody radiation and corrected for ambient and other temperatures. The ratio or difference of the two measurements may have been previously correlated to a concentration of the substance in the blood using invasive measurement methods. Hence, the two measurements may be used to determine the concentration of the substance.

During measurement of the IR radiation emission of a blackbody (such as for calibration) and of a body (such as human or animal subjects), fluctuations in radiation emission might significantly impact the accuracy of substance concentration measurements. Fluctuations might also prevent substance concentration measurements within the accuracy of definitions promulgated by medical regulatory entities (e.g., the US Food and Drug Administration). By measuring device emissions as reflected from a mirror through a filter with the same spectral characteristics (immediately after blackbody or body measurement) and including these mirror measurements in a substance estimation algorithm, the accuracy of substance estimation may increase by an order of magnitude.

As one example, if we consider the thermal state of a thermopile-type of IR detector (with a hot and cold junction) in equilibrium when measuring a signal from the skin, then the thermal equilibrium equation can be modeled as:

$$A+kS(T)=k(T_h-T_c)+kT_h^4+k(T_h-T_g) \text{ where:} \quad (1)$$

A is the signal received from the body by the sensitive area of the detector; S(T) is a temperature-based function that represents aggregate emission from all components of the system that are hitting the sensitive area of the detector (i.e., the hot junction);
$T_h$ is the detector hot junction temperature;
$T_c$ is the detector cold junction temperature; and
$T_g$ is the temperature of the gas inside the detector.

Throughout this document, "k" represents a generic constant k, not the same specific constant in each instance that it appears. For example, the k in front of $(T_h-T_c)$ in Equation 1 does not necessarily have the same value as the k in front of $T_h^4$. Although Equation 1 models a thermopile detector, it will be appreciated that an analogous equation and something similar to the following derivation might be prepared for other types of IR detectors to implement the concepts herein described.

We can also model the voltage output of the detector as $$V_{out}=k(T_h-T_c) \quad (2)$$

Combining Equations 1 and 2 we can write $$V_{out}=kA+kS(T)-kT_h^4-k(T_h-T_g) \quad (3)$$

If we assume that the cold junction temperature is the same as the temperature of the gas $(T_h-T_g)$ then $k(T_h-T_g)$ can be combined with $k(T_h-T_c)$ in Equation 1 (with propagation of constants) and rewrite Equation 3 as $$V_{out}=kA+kS(T)-kT_h^4 \quad (4)$$

or $$A=kV_{out}-kS(T)+kT_h^4 \quad (4')$$

If we now consider the thermal state of the detector when measuring a signal from the mirror, the thermal equilibrium equation can be modeled as $$MR+CS(T)=C(T_h-T_c)+CT_h^4 \quad (5)$$

where MR is the reflected signal received from the mirror by the sensitive area of the detector and C replaces k as a generic constant in the mirror equations. Again, we assumed that the cold junction temperature is the same as the temperature of the gas $(T_h-T_g)$ then $C(T_h-T_g)$ was combined with $C(T_h-T_c)$ as above, though the steps of combining are omitted.

We can now write voltage output of the detector $V_m$ during mirror reflection as:

$$V_m=CMR+CS(T)-CT_h^4 \quad (6)$$

Since $MR=f(CT_h^4+CS(T))$ as the mirror reflects the aggregate emission from all components of the system, $$V_m \text{ can be written as } CS(T)-CT_h^4 \quad (7)$$

We now have two signals, namely, $V_{out}$ from Equation (4) and $V_m$ from Equation (7). Combining these two voltage signals, we have $$V_{out}-CV_m=kA+(k-C)S(T)-(k-C)T_h^4 \quad (8)$$

The goal is to use a blackbody, such as is known for use in calibration, to find constant C where the coefficient in front of S(T) minus the coefficient in front of $T_h^4$ enables them to cancel. This leaves $$A=kV_{out}-CV_m \quad (9)$$

This is practically achieved by minimizing the error in a best fit calculation over a variety of ambient temperatures and blackbody temperatures (which simulate emission from the body). Once the constant is calculated it is stored in device memory and used to correct glucose measurements.

Accordingly, the calculated constant may be used in various methods and systems described herein for correcting substance concentrations. One substance concentration correction system includes an infrared radiation detector having a sensitive area that receives infrared radiation from a body external to the correction system. The system also includes components that produce an aggregate emission of infrared radiation, a first portion of the aggregate emission being incident on the sensitive area. The system further includes a mirror assembly including a mirror and being changeable between a correcting configuration and a measuring configuration. Thus, in the correcting configuration, a second portion of the aggregate emission is reflected by the mirror, which produces a mirror signal incident on the sensitive area. The mirror assembly also obstructs the external body infrared radiation from reaching the sensitive area. In the measuring configuration, the mirror assembly allows the external body infrared radiation onto the sensitive area.

By way of example, the system may further include a filter assembly including a peak filter and a reference filter. The filter assembly may be selectively alignable with the detector so that the external body infrared radiation passes through the peak filter in the measuring configuration and the mirror signal passes through the same peak filter in the correcting configuration. The filter assembly may also be selectively alignable with the detector so that the external body infrared radiation passes through the reference filter in the measuring configuration and the mirror signal passes through the same reference filter in the correcting configuration.

The system may include a controller programmed to perform operations such as automatically changing the mirror assembly between the correcting configuration and the measuring configuration and automatically changing the filter assembly between the peak filter and the reference filter. A housing may enclose the detector, the components, and the mirror assembly and have an optical aperture through which passes the external body infrared radiation incident on the sensitive area. The mirror assembly may obstruct the optical aperture when in the correcting configuration. The mirror assembly may include a rotatable platform connected to the mirror and a motor connected to the platform. Actuation of the motor rotates the platform and pivots the mirror between the correcting configuration and the measuring configuration.

The components that produce the aggregate emission may include an optical assembly with a lens and a filter assembly with a filter. The external body infrared radiation passes through the lens and the filter in the measuring configuration and the mirror signal passes through the same lens and the same filter in the correcting configuration. As one example, the filter assembly may include a peak filter connected to a rotatable platform, a reference filter connected to the platform, and a motor connected to the platform. Actuation of the motor rotates the platform and pivots between the peak filter and the reference filter being aligned with the detector. As another example, the filter assembly may include a rotatable wheel with a peak filter attached to a portion of the wheel and a reference filter attached to another portion of the wheel. In such case, the mirror assembly may include one mirror attached to the wheel and overlapping a portion of the peak filter and another mirror attached to the wheel and overlapping a portion of the reference filter.

The system may include a signal processing unit programmed to perform operations. One operation includes recording a measurement of the external body infrared radiation at the sensitive area while the mirror assembly is in the measuring configuration. Another operation includes recording a measurement of the reflected, aggregate emission at the sensitive area while the mirror assembly is in the correcting configuration. A further operation includes calculating a substance concentration in the body based on the measurement in the measuring configuration and correcting the substance concentration in the body based on the measurement in the correcting configuration.

Another substance concentration correction system includes an infrared radiation detector having a sensitive area that receives infrared radiation from a body external to the correction system. The system also includes a filter assembly and an optical assembly that produce an aggregate emission of infrared radiation, a first portion of the aggregate emission being incident on the sensitive area. The system further includes a mirror assembly including a mirror and being changeable between a correcting configuration and a measuring configuration. Thus, in the correcting configuration, a second portion of the aggregate emission is reflected by the mirror, which produces a mirror signal incident on the sensitive area. The mirror assembly also obstructs the external body infrared radiation from the sensitive area. In the measuring configuration, the mirror assembly allows the external body infrared radiation onto the sensitive area.

The filter assembly includes a peak filter and a reference filter selectively alignable with the detector. Thus, the external body infrared radiation passes through the peak filter in the measuring configuration and the mirror signal passes through the same peak filter in the correcting configuration. Also, the external body infrared radiation passes through the reference filter in the measuring configuration and the mirror signal passes through the same reference filter in the correcting configuration. The optical assembly includes a lens configured so that the external body infrared radiation passes through the lens in the measuring configuration and the mirror signal passes through the same lens in the correcting configuration. A housing encloses the detector, the filter assembly, the optical assembly, and the mirror assembly. The housing has an optical aperture through which passes the external body infrared radiation incident on the sensitive area, wherein the mirror assembly obstructs the optical aperture when in the correcting configuration.

By way of example, the mirror assembly includes a rotatable platform connected to the mirror in an orientation normal to the mirror and a motor connected to the platform. Actuation of the motor rotates the platform and pivots the mirror between the correcting configuration and the measuring configuration. As another example, the mirror assembly includes a wheel rotatable within a wheel plane, the mirror assembly including one mirror attached to the wheel and overlapping a portion of the peak filter and another mirror attached to the wheel and overlapping a portion of the reference filter. The mirror and the other mirror lying in planes parallel to the wheel plane.

A substance concentration correction method includes providing a substance concentration correction system having an infrared radiation detector having a sensitive area, components that produce an aggregate emission of infrared radiation, a mirror assembly including a mirror. Instead, another system described herein may be provided. The method includes placing the mirror assembly in a measuring configuration. As enabled by the measuring configuration, the method includes receiving infrared radiation on the sensitive area from a body external to the correction system and simultaneously receiving a first portion of the aggregate emission on the sensitive area. A measurement value corresponding to the external body infrared radiation combined with the first portion of the aggregate emission is recorded from the detector. The measurement value is indicative of a substance concentration.

The method includes placing the mirror assembly in a correcting configuration. As enabled by the correcting configuration, the method includes reflecting a second portion of the aggregate emission with the mirror, which produces a mirror signal incident on the sensitive area, and the mirror assembly simultaneously obstructing the external body infrared radiation from the sensitive area. A correction value corresponding to the mirror signal is recorded from the detector. The method includes correcting the measurement value based on the correction value and calculating the substance concentration based on the corrected measurement value.

By way of example, the correction system may further include a filter assembly with a peak filter and a reference filter. Thus, the method may also include aligning the peak filter with the detector, passing the external body infrared radiation through the peak filter in the measuring configuration, and passing the mirror signal through the same peak filter in the correcting configuration. The method may further include aligning the reference filter with the detector, passing the external body infrared radiation through the reference filter in the measuring configuration, and passing the mirror signal through the same reference filter in the correcting configuration.

A controller may be activated that automatically changes the mirror assembly between the correcting configuration and the measuring configuration by actuating a motor and automatically changes the filter assembly between the peak filter and the reference filter by actuating another motor.

The filter assembly may include a rotatable wheel with the peak filter attached to a portion of the wheel and the reference filter attached to another portion of the wheel. The mirror assembly may include one mirror attached to the wheel and overlapping a portion of the peak filter and another mirror attached to the wheel and overlapping a portion of the reference filter. Automatically changing the mirror assembly and automatically changing the filter assembly may both include continuously rotating the filter wheel in one direction.

As described further herein, calculating the substance concentration may use an empirically-derived correlation table.

Figure 1:
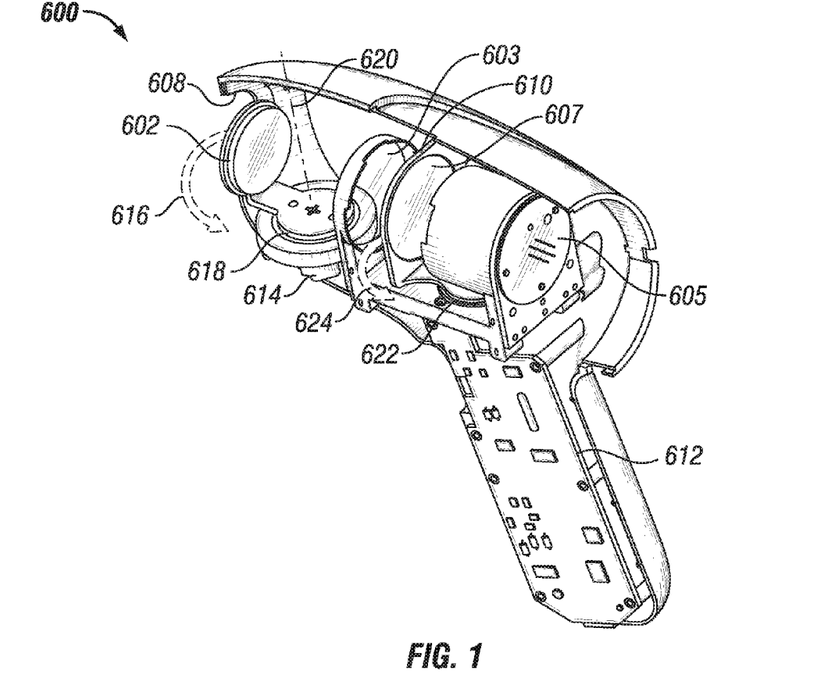
FIG. 1 is a perspective, partial cut-away view of system for correcting non-invasive substance concentration measurements depicted as a handheld meter with a mirror.

FIG. 1 shows one example of a substance concentration correction system 600 that measures and corrects a concentration of a substance in a body. System 600 may include components of and operate in accordance with U.S. patent application Ser. No. 12/883,063 incorporated herein. System 600 includes an infrared detector 605, such as a thermopile detector. Infrared detector 605 may detect light within the MIR range. System 600 further includes an optical assembly 603 to focus received MIR radiation on a sensing surface of infrared detector 605. Optical assembly 603 is shown in FIG. 1 including a lens.

System 600 also includes a filter assembly with a filter 607 mounted in a filter holder 610 in turn connected to a rotatable platform 622. Filter 607 may be an interference filter and is shown in alignment with detector 605. Although not apparent in FIG. 1, the filter assembly includes another filter mounted in another filter holder in turn connected to platform 622 and a motor (not shown) connected to the platform. The motor rotates platform 622 about an axis (not shown) parallel with axis 620 to move filter 607 in direction 624 out of alignment with detector 605 and to move the other filter into alignment with detector 605. The rotation may be about 90 degrees. Filter 607 may be a bandpass filter passing a signal with a wavelength where glucose has peak emission/absorption (a peak filter). The other filter may be a bandpass filter passing a signal with a wavelength where glucose has negligible emission/absorption (a reference filter).

System 600 also includes a mirror assembly with a mirror 602 connected to a rotatable platform 618 in turn connected to a motor 614. Motor 614 rotates platform 618 about axis 620 and pivots mirror 602 in direction 616 between a correcting configuration shown in FIG. 1 and a measuring configuration. The rotation may be about 90 degrees. In the correcting configuration, aggregate emission from components of system 600 may be reflected by the mirror, which produces a mirror signal to detector 605. The mirror assembly may also obstruct external body infrared radiation from reaching the sensitive area.

System 600 includes a housing enclosing detector 605, the filter assembly, the optical assembly, the mirror assembly, and other components and having an optical aperture 608 through which passes the external body infrared radiation directed to detector 605. In the measuring configuration, the mirror assembly allows the external body infrared radiation onto the sensitive area of detector 605 when mirror 602 is moved out of view of optical aperture 608. After a measurement with filter 607 or the other filter, mirror 602 may be moved into view of optical aperture 608 and a measurement of the mirror may be made through the same filter assembly and through the same optical assembly 603.

During operation, system 600 may record at least one MIR measurement of a surface of a body through optical assembly 603. For example, a first MIR measurement may be taken in a first wavelength band in which a substance has an effect on MIR emission or absorption and a second MIR measurement may be taken in a second wavelength band in which the substance has no or negligible effect on MIR emission or absorption. System 600 may record an MIR measurement of the mirror 602 through optical assembly 603. The MIR measurement of mirror 602 may be taken for the first wavelength band and for the second wavelength band using the filter assembly.

Figure 3:
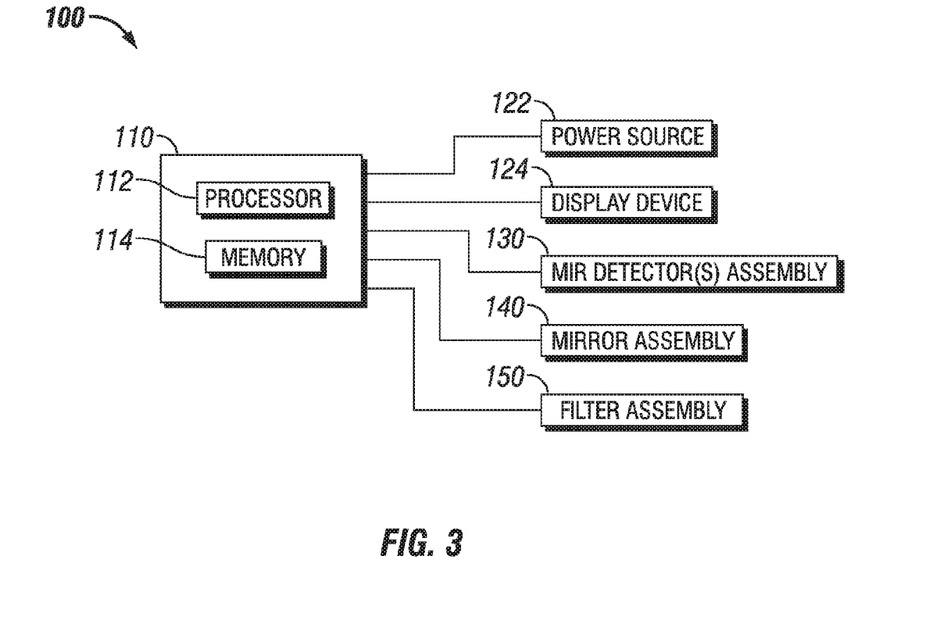
FIG. 3 is a block diagram of a system for correcting non-invasive substance concentration measurements.

System 600 includes circuitry 612 to implement control and signal processing functions. FIG. 3 shows a block diagram of a substance concentration correction system 100 with features that may be implemented using circuitry 612. System 100 includes a controller 110, a power source 122, a display device 124, a mid-infrared (MIR) detector assembly 130, a mirror assembly 140, and a filter assembly 150. MIR detector 130 may include a preassembled sensor and an optical element. For example, the optical element may include a lens, and may focus IR radiation on the sensor in order to detect the radiation. The optical element may instead be a window.

Controller 110 includes a processor 112 and a memory 114. Processor 112 may include circuitry capable of receiving and processing signals. Memory 114 may be accessible to processor 112 to enable processor 112 to retrieve data from memory 114 and to store data at memory 114. To illustrate, memory 114 may include a processor readable medium that may store instructions that, when executed by the processor, cause the processor to perform operations as described herein.

Power source 122 may provide power to controller 110, display device 124, MIR detector assembly 130, and the motors of the mirror and filter assemblies. Power source 122 may hold a charge for extended durations to enable long term portability. For example, power source 122 may be capable of powering system 100 for one or more days without being recharged. As an example, power source 122 may include a rechargeable lithium ion battery pack.

Display device 124 may include any device capable of outputting visual or audio signals to a user of system 100. For example, the display device may include a liquid crystal diode (LCD) screen, a buzzer, another type of visual or audio output device, or any combination thereof. Although FIG. 1 depicts system 100 as including display device 124, system 100 may omit the display device 124. As an example, system 100 may rely on a wireless transmission to a remote device to generate user outputs.

MIR detector assembly 130 may include devices capable of detecting MIR emission and/or absorption within one or more wavelength bands. For example, for glucose, the peak wavelength band may be about 9.3 µm to about 9.9 µm. For glucose, the reference wavelength band may be about 10.5 µm to about 15 µm. The MIR detector assembly 130 may be further configured to measure the MIR emission and/or absorption of one or more blackbody devices.

Figure 2:
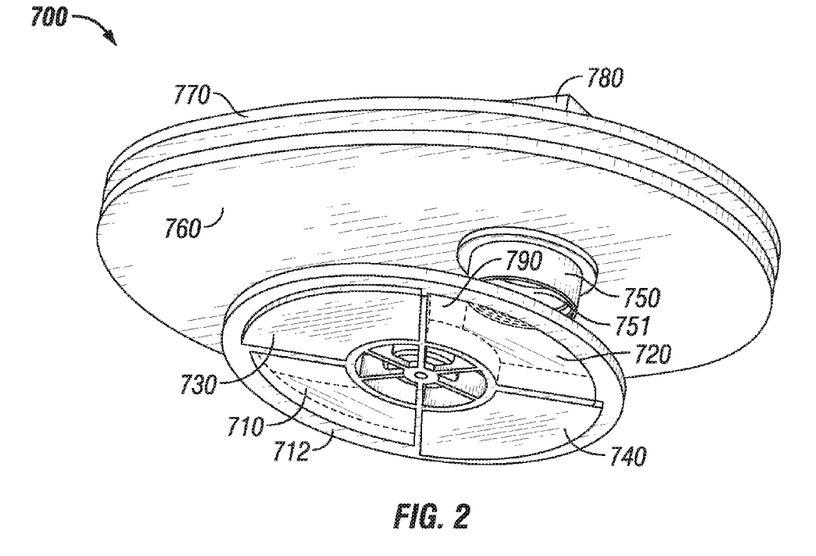
FIG. 2 is a perspective view of another system for correcting non-invasive substance concentration measurements depicted as one component of wearable monitor with a mirror. The monitoring may occur continuously.

FIG. 2 shows a substance concentration correction system 700 adapted for use with wearable non-invasive substance concentration systems and methods, such as in the '180 application discussed above. System 700 includes electronic circuitry 760, a detector 750, and a filter wheel 712. Electronic circuitry 760 (e.g., a printed circuit board) may include units associated with control and/or signal processing. For example, electronic circuitry 760 may include a controller, such as controller 110. It follows that substance concentration correction system 100 may be implemented using electronic circuitry 760.

Detector 750 may be electrically connected to electronic circuitry 760 and may be configured to detect MIR radiation. Further, detector 750 may include optical assembly 751 to focus or otherwise adjust received MIR radiation for detection.

Filter wheel 712 may include two or more filters 710, 720. Each of filters 710, 720 may cover sections of approximately 180 degrees of filter wheel 712. The function of the first and second filters may be as respective peak and reference filters. Half of each filter may be covered by mirrors 730 and 740. Filters 710, 720 may have arcuate shapes. Detector 750 and motor 790 may be mechanically connected to a chassis 770. Electronic circuitry 760, detector 750 and wheel motor 790 may be powered by chargeable battery 780.

Perturbations associated with MIR measurements taken at the detector 750 may be corrected by measuring the MIR radiation emission reflected from mirrors 730, 740. The mirror measurement may be taken immediately after each signal measurement to enhance the accuracy of the correction. For example, detector 750 with optical assembly 751 may alternate measuring (or cycle measuring) between a body emission received through first filter 710, a mirror reflection passing through first filter 710, a body emission received through second filter 720, and a mirror reflection passing through second filter 720. The mirror reflection measurements may be used to correct non-invasive substance concentration signal measurements taken in the MIR region.

It will be understood that the details of features described with respect to individual systems and methods may be used in like features of the other systems and methods described herein as consistent and appropriate even though not otherwise expressly indicated.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

TABLE OF REFERENCE NUMERALS FOR FIGURES

| | |
|---|---|
| 100 | system |
| 110 | controller |
| 112 | processor |
| 114 | memory |
| 122 | power source |
| 124 | display device |
| 130 | MIR detector assembly |
| 140 | mirror assembly |
| 150 | filter assembly |
| 600 | system |
| 602 | mirror |
| 603 | optical assembly |
| 605 | infrared detector |
| 607 | filter |

-continued

TABLE OF REFERENCE NUMERALS FOR FIGURES

| | |
|---|---|
| 608 | optical aperture |
| 610 | filter holder |
| 612 | circuitry |
| 614 | motor |
| 616 | direction |
| 618 | platform |
| 620 | axis |
| 622 | platform |
| 624 | direction |
| 700 | system |
| 710 | first filter |
| 712 | filter wheel |
| 720 | second filter |
| 730 | mirror |
| 740 | mirror |
| 750 | detector |
| 751 | optical assembly |
| 760 | circuitry |
| 770 | chassis |
| 780 | battery |
| 790 | motor |

What is claimed is:

1. A substance concentration correction system comprising:
    an infrared radiation detector having a sensitive area that receives infrared radiation from a body external to the correction system;
    a filter assembly and an optical assembly that produce an aggregate emission of infrared radiation, a first portion of the aggregate emission being incident on the sensitive area;
    a mirror assembly including a mirror and being changeable between a correcting configuration and a measuring configuration so that, in the correcting configuration, a second portion of the aggregate emission is reflected by the mirror, which produces a mirror signal incident on the sensitive area, and the mirror assembly obstructs the external body infrared radiation from reaching the sensitive area and, in the measuring configuration, the mirror assembly allows the external body infrared radiation onto the sensitive area;
    the filter assembly including a peak filter passing a peak signal with a wavelength where the substance has peak emission/absorption and a reference filter passing a reference signal with a wavelength where the substance has negligible emission/absorption, the peak filter and the reference filter being selectively alignable with the detector so that the external body infrared radiation passes through the peak filter in the measuring configuration for the peak signal and the mirror signal passes through the same peak filter in the correcting configuration for the peak signal and so that the external body infrared radiation passes through the reference filter in the measuring configuration for the reference signal and the mirror signal passes through the same reference filter in the correcting configuration for the reference signal; and
    the optical assembly being configured so that the external body infrared radiation passes through the optical assembly in the measuring configuration for the peak and reference signals and the mirror signal passes through the same optical assembly in the correcting configuration for the peak and reference signals.

2. The system of claim 1 further comprising a controller programmed to perform operations including automatically changing the mirror assembly between the correcting configuration and the measuring configuration and automatically changing the filter assembly between the peak filter and the reference filter.

3. The system of claim 1 further comprising a housing enclosing the detector, the filter assembly, the optical assembly, and the mirror assembly and having an optical aperture through which passes the external body infrared radiation incident on the sensitive area, wherein the mirror assembly obstructs the optical aperture when in the correcting configuration.

4. The system of claim 1 wherein the mirror assembly comprises a rotatable mirror platform connected to the mirror and a mirror motor connected to the mirror platform and wherein actuation of the mirror motor rotates the mirror platform and pivots the mirror between the correcting configuration and the measuring configuration.

5. The system of claim 4 wherein the mirror platform is connected to the mirror in an orientation normal to the mirror.

6. The system of claim 1 wherein the optical assembly includes a lens and the external body infrared radiation passes through the lens in the measuring configuration and the mirror signal passes through the same lens in the correcting configuration.

7. The system of claim 6 wherein the peak filter is connected to a rotatable filter platform, the reference filter is connected to the filter platform, and the filter assembly further comprises a filter motor connected to the filter platform and actuation of the filter motor rotates the filter platform and pivots between the peak filter and the reference filter being aligned with the detector.

8. The system of claim 6 wherein the filter assembly comprises a rotatable wheel with the peak filter attached to a portion of the wheel and the reference filter attached to another portion of the wheel.

9. The system of claim 8 wherein the mirror assembly comprises one mirror attached to the wheel and overlapping a portion of the peak filter and another mirror attached to the wheel and overlapping a portion of the reference filter.

10. The system of claim 9 wherein the wheel is rotatable within a wheel plane, the mirror and the other mirror lying in planes parallel to the wheel plane.

11. The system of claim 1 further comprising a signal processing unit programmed to perform operations including:
  recording a measurement of the external body infrared radiation at the sensitive area while the mirror assembly is in the measuring configuration for the peak signal and in the measuring configuration for the reference signal;
  recording a measurement of the reflected, aggregate emission at the sensitive area while the mirror assembly is in the correcting configuration for the peak signal and in the correcting configuration for the reference signal; and
  calculating a substance concentration in the body based on the measurement in the measuring configuration for the peak signal and for the reference signal and correcting the substance concentration in the body based on the measurement in the correcting configuration for the peak signal and for the reference signal.

12. A substance concentration correction system comprising:
  an infrared radiation detector having a sensitive area that receives infrared radiation from a body external to the correction system;
  a filter assembly and an optical assembly that produce an aggregate emission of infrared radiation, a first portion of the aggregate emission being incident on the sensitive area;
  a mirror assembly including a mirror and being changeable between a correcting configuration and a measuring configuration so that, in the correcting configuration, a second portion of the aggregate emission is reflected by the mirror, which produces a mirror signal incident on the sensitive area, and the mirror assembly obstructs the external body infrared radiation from reaching the sensitive area and, in the measuring configuration, the mirror assembly allows the external body infrared radiation onto the sensitive area;
  the filter assembly including a peak filter passing a peak signal with a wavelength where the substance has peak emission/absorption and a reference filter passing a reference signal with a wavelength where the substance has negligible emission/absorption, the peak filter and the reference filter being selectively alignable with the detector so that the external body infrared radiation passes through the peak filter in the measuring configuration for the peak signal and the mirror signal passes through the same peak filter in the correcting configuration for the peak signal and so that the external body infrared radiation passes through the reference filter in the measuring configuration for the reference signal and the mirror signal passes through the same reference filter in the correcting configuration for the reference signal;
  the optical assembly including a lens configured so that the external body infrared radiation passes through the lens in the measuring configuration for the peak and reference signals and the mirror signal passes through the same lens in the correcting configuration for the peak and reference signals;
  a housing enclosing the detector, the filter assembly, the optical assembly, and the mirror assembly and having an optical aperture through which passes the external body infrared radiation incident on the sensitive area, wherein the mirror assembly obstructs the optical aperture when in the correcting configuration.

13. The system of claim 12 wherein the mirror assembly comprises a rotatable mirror platform connected to the mirror in an orientation normal to the mirror and a mirror motor connected to the mirror platform and wherein actuation of the mirror motor rotates the mirror platform and pivots the mirror between the correcting configuration and the measuring configuration.

14. The system of claim 12 wherein the mirror assembly comprises a wheel rotatable within a wheel plane, the mirror assembly including one mirror attached to the wheel and overlapping a portion of the peak filter and another mirror attached to the wheel and overlapping a portion of the reference filter, the mirror and the other mirror lying in planes parallel to the wheel plane.

15. A substance concentration correction method comprising:
  providing a substance concentration correction system including:
    an infrared radiation detector having a sensitive area;
    a filter assembly and an optical assembly that produce an aggregate emission of infrared radiation;
    a mirror assembly including a mirror; and
    the filter assembly including a peak filter passing a peak signal with a wavelength where the substance has peak emission/absorption and a reference filter passing a reference signal with a wavelength where the substance has negligible emission/absorption;

placing the mirror assembly in a measuring configuration;

aligning the peak filter with the detector;

as enabled by the measuring configuration, passing infrared radiation through the optical assembly and the peak filter from a body external to the correction system, receiving peak filtered external body infrared radiation on the sensitive area, and simultaneously receiving a peak filtered first portion of the aggregate emission on the sensitive area;

recording a peak measurement value from the detector corresponding to the peak filtered external body infrared radiation combined with the peak filtered first portion of the aggregate emission, the peak measurement value being indicative of a substance concentration;

placing the mirror assembly in a correcting configuration;

as enabled by the correcting configuration, reflecting a second portion of the aggregate emission with the mirror, which produces a mirror signal passing through the optical assembly and the peak filter and incident on the sensitive area, and the mirror assembly simultaneously obstructing the external body infrared radiation from the sensitive area;

recording a peak correction value from the detector corresponding to the peak filtered mirror signal and correcting the peak measurement value based on the peak correction value;

aligning the reference filter with the detector;

as enabled by the measuring configuration, passing the external body infrared radiation through the optical assembly and the reference filter, receiving reference filtered external body infrared radiation on the sensitive area, and simultaneously receiving a reference filtered first portion of the aggregate emission on the sensitive area;

recording a reference measurement value from the detector corresponding to the reference filtered external body infrared radiation combined with the reference filtered first portion of the aggregate emission;

placing the mirror assembly in a correcting configuration;

as enabled by the correcting configuration, reflecting a second portion of the aggregate emission with the mirror, which produces a mirror signal passing through the optical assembly and the reference filter and incident on the sensitive area, and the mirror assembly simultaneously obstructing the external body infrared radiation from the sensitive area;

recording a reference correction value from the detector corresponding to the reference filtered mirror signal and correcting the reference measurement value based on the reference correction value; and calculating the substance concentration based on the corrected peak measurement value and on the corrected reference measurement value.

16. The method of claim 15 further comprising activating a controller that automatically changes the mirror assembly between the correcting configuration and the measuring configuration by actuating a motor and automatically changes the filter assembly between the peak filter and the reference filter by actuating another motor.

17. The method of claim 16 wherein the filter assembly comprises a rotatable wheel with the peak filter attached to a portion of the wheel and the reference filter attached to another portion of the wheel and the mirror assembly comprises one mirror attached to the wheel and overlapping a portion of the peak filter and another mirror attached to the wheel and overlapping a portion of the reference filter and wherein automatically changing the mirror assembly and automatically changing the filter assembly both comprise continuously rotating the filter wheel in one direction.

18. The method of claim 15 wherein calculating the substance concentration uses an empirically-derived correlation table.

* * * * *